(12) United States Patent
Imran et al.

(10) Patent No.: US 11,642,438 B2
(45) Date of Patent: May 9, 2023

(54) BIODEGRADABLE MEDICAL IMPLANTS, POLYMER COMPOSITIONS AND METHODS OF USE

(71) Applicant: InCube Labs, LLC, San Jose, CA (US)

(72) Inventors: Mir Imran, Los Altos Hills, CA (US); Sanjay Patel, San Diego, CA (US); Joel Harris, Mountain View, CA (US)

(73) Assignee: InCube Labs, LLC, San Jose, CA (US)

( * ) Notice: Subject to any disclaimer, the term of this patent is extended or adjusted under 35 U.S.C. 154(b) by 1142 days.

(21) Appl. No.: 16/035,504

(22) Filed: Jul. 13, 2018

(65) Prior Publication Data

US 2018/0353641 A1   Dec. 13, 2018

Related U.S. Application Data

(62) Division of application No. 13/261,054, filed as application No. PCT/US2010/001609 on Jun. 1, 2010, now Pat. No. 10,046,085.

(Continued)

(51) Int. Cl.
| | | |
|---|---|---|
| *A61L 27/14* | (2006.01) | |
| *A61F 2/82* | (2013.01) | |

(Continued)

(52) U.S. Cl.
CPC ............ *A61L 27/14* (2013.01); *A61F 2/04* (2013.01); *A61F 2/82* (2013.01); *A61L 27/26* (2013.01);

(Continued)

(58) Field of Classification Search
CPC ...... A61F 2/04; A61F 2/06; A61F 2/07; A61F 2/82; A61L 27/26; A61L 27/58; A61L 31/041; A61L 31/148; A61L 27/14

See application file for complete search history.

(56) References Cited

U.S. PATENT DOCUMENTS

| 6,368,356 B1 | 4/2002 | Zhong et al. |
| 10,046,085 B2 | 8/2018 | Imran et al. |

(Continued)

FOREIGN PATENT DOCUMENTS

WO   WO-2010138212 A2   12/2010

OTHER PUBLICATIONS

De Soussa et al. Analysis of Tensile Strength of Poly(lactic-co-glycolic acid) Membranes Used for Guided Tissue Regeneration. RSBO. 2014 11(1): 59-65.

(Continued)

*Primary Examiner* — Jerrah Edwards
*Assistant Examiner* — Rokhaya Diop
(74) *Attorney, Agent, or Firm* — Brooks Kushman P.C.

(57) ABSTRACT

Embodiments of the invention provide compositions including bio degradable polymers, medical implants fabricated from these compositions and methods of using such implants. Many embodiments provide medical implants comprising a first polymer backbone having a first rate of biodegradation and a second polymer backbone having a second rate of biodegradation faster than the first rate. In some embodiments, the second backbone is configured to be replaced by a natural tissue layer. The first backbone provides a scaffold for the implant while the second backbone degrades. This scaffold can enhance mechanical properties of the implant including various aspects of mechanical strength such as tensile, bending, hoop and yield strength; and elasticity. The scaffold also serves to maintain a minimum level of structural support of the implant during the period of degradation of the second backbone or for the entire life of the implant so that the implant does not mechanically fail.

29 Claims, 3 Drawing Sheets

Related U.S. Application Data

(60) Provisional application No. 61/217,345, filed on May 29, 2009.

(51) Int. Cl.

| | | |
|---|---|---|
| *A61L 27/26* | (2006.01) | |
| *A61L 27/58* | (2006.01) | |
| *A61L 31/04* | (2006.01) | |
| *A61L 31/14* | (2006.01) | |
| *A61F 2/04* | (2013.01) | |
| *A61F 2/06* | (2013.01) | |
| *A61F 2/07* | (2013.01) | |

(52) U.S. Cl.
CPC ............ *A61L 27/58* (2013.01); *A61L 31/041* (2013.01); *A61L 31/148* (2013.01); *A61F 2/06* (2013.01); *A61F 2/07* (2013.01); *A61F 2210/0004* (2013.01)

(56) References Cited

U.S. PATENT DOCUMENTS

| | | |
|---|---|---|
| 2003/0072790 A1 | 4/2003 | Tsai et al. |
| 2005/0021131 A1 | 1/2005 | Venkatraman et al. |
| 2005/0042253 A1 | 2/2005 | Farrar et al. |
| 2005/0063937 A1 | 3/2005 | Li et al. |
| 2006/0094017 A1 | 5/2006 | Conley et al. |
| 2007/0299510 A1 | 12/2007 | Venkatraman et al. |
| 2008/0015686 A1 | 1/2008 | Gale et al. |
| 2010/0023132 A1 | 1/2010 | Imran |

OTHER PUBLICATIONS

Eastman_Properties of Polyurethane Thermoset Elastomer_http://plastics.ides.com/generics/57/c/t/polyurethane-thermoset-elastomer-tsu-properties-processing Accesed Sep. 26, 2014.

Gentile et al. An Overview of Poly(lactic-co-glycolic acid)-Based Materials for Bone Tissue Engineering. Int. J. Mol. Sci. 2014 (15):3640-3659.

International search report and written opinion dated Feb. 25, 2011 for PCT/US2010/001609.

Notice of Allowance dated Apr. 9, 2018 for U.S. Appl. No. 13/261,054.

Office Action dated Apr. 7, 2016 for U.S. Appl. No. 13/261,054.

Office action dated Jul. 14, 2015 for U.S. Appl. No. 13/261,054.

Office action dated Oct. 7, 2014 for U.S. Appl. No. 13/261,054.

Office Action dated Dec. 12, 2016 for U.S. Appl. No. 13/261,054.

Rowlands et al. Polyurethane/Poly(lactic-co-glycolic) Acid Composite Scaffolds Fabricated by Thermally Induced Phase Separation. Biomaterials, 28 (2007):2109-2121.

BIODEGRADABLE MEDICAL IMPLANTS, POLYMER COMPOSITIONS AND METHODS OF USE

CROSS-REFERENCE TO RELATED APPLICATIONS

This application is a divisional of U.S. patent application Ser. No. 13/261,054, filed Aug. 21, 2013, now U.S. Pat. No. 10,046,085, which is a National Stage Entry of PCT Application No. PCT/US10/01609, filed Jun. 1, 2010, which claims the benefit of Provisional No. 61/217,345, filed May 29, 2009, the entire contents of which are incorporated herein by reference.

BACKGROUND OF THE INVENTION

1. Field of the Invention

Embodiments of invention relate to polymer compositions for implanted medical devices. More specifically, embodiments of the invention relate to a polymer composition comprising differentially degradable polymers; implanted medical devices using such polymer compositions and methods of using such implanted devices.

A number or polymer-based medical devices have been developed for implantation in the human body. These include vascular grafts, stents, scaffolds structures, heart valves artificial joints, surgical meshes for reconstructive surgery and other devices. Many of these devices use polymers which remain stable in the body over time with little or no chemical or structural degradation. Others devices such as sutures use biodegradable material which degrades over time as result of hydrolysis and other chemical reactions in the body. Such devices can include sutures, vascular grafts and various scaffold structures. While current degradable materials offer advantages by allowing the body to replace the material with natural tissue and reduce the potential for a foreign body response, they also can have limitations in their material properties including lack of elasticity, tensile strength, yield strength, etc. Also in some cases it may desirable to have a small amount of polymer material remain to provide long term structural support for a particular implant site such as an artery or in an intestinal anastomoses. Thus, there is a need for biodegradable polymers and associated devices which also have improved material properties for long term implantation.

BRIEF SUMMARY OF THE INVENTION

Embodiments of the invention provide compositions comprising bio degradable polymer mixtures, medical implants fabricated from these compositions and methods of using such implants. Various embodiments provide such compositions and implants that have material and mechanical properties tailored for a particular implant site(s) and/or function(s). Many embodiments provide medical implants fabricated from a composition comprising a first polymer backbone having a first rate of bio-degradation and a second polymer backbone having a second rate of biodegradation faster than first rate of biodegradation. In some embodiments, the second polymer backbone is ultimately replaced by a natural layer of tissue such as endothelial cells. The first polymer backbone provides a scaffold for the implant while the second polymer backbone degrades. This scaffold can enhance one or more mechanical properties of the implant including various aspects of mechanical strength such as tensile strength, bending strength and hoop strength; elasticity and yield strength; and fracture resistance. One or more of these properties can serve to reduce the likelihood of mechanical failure of the implant. The scaffold also serves to maintain a minimum level of structural rigidity and/or support of the implant during the period of degradation of the second backbone or for the entire life of the implant. This allows the implant to continue to perform one or more of its intended functions during the period of degradation. Such functions can include, for example, providing support for a surgical anastomosis in the GI tract, or maintaining the patency of an artery, vein or a duct until such time the second backbone is replaced with cellular tissue or, if necessary, for the life of the implant.

In many embodiments, the first polymer backbone has a substantially stable structure within the body during the life of the implant, or otherwise may have a substantially slower rate of biodegradation such that scaffold is still substantially in place after the second backbone has completely degraded. The first and second backbones may also have selected amounts of cross linking with the amount of cross linking selected to slow or otherwise control the rate of biodegradation of one or both of the first or second backbones. Over time, the second backbone is broken down by chemical reactions within the body such as hydrolysis, while the first backbone remains or substantially remains. The rate of degradation can be controlled by one or more of the following factors: i) the chemical nature of the first and second backbone and the physical properties resulting therefrom (e.g., the types of chemical linkages within the backbone and the functional groups attached to the backbone; crystallinity, hydrophilicity, etc); ii) the weight ratio of the first backbone to the second backbone; iii) the presence or absence of cross-linking between the backbones; and iv) an amount of cross linking of the backbones, with greater amounts of cross linking providing slower rates of degradation. One or more of these factors such as the amount of cross linking, can be selected to control one or both the rates of degradation of the first and the second backbone.

In preferred embodiments, the first polymer backbone comprises polyurethane (PU) and the second polymer backbone comprises polyglycolic lactic acid (PGLA); however, other materials are also contemplated. The ratio of PU to PGLA can be in the range of about 1:20 to 20:1, with specific embodiments of 1:4, 2:3, 1:1, 3:2 and 4:1. Higher amounts of PU can be selected for medical implant applications requiring increased mechanical strength such as tensile strength for GI applications and hoop strength for vascular application. Ratios of about 1:1 or 1:2 can be selected for application requiring a combination of good strength and elasticity.

Embodiments of the polymer compositions described herein can be used for the fabrication of a number of biodegradable medical implants. These can include vascular implants such as vascular grafts (e.g., an aortic graft), arterial stents (e.g., coronary arterial stents), or heart valves; gastro-intestinal implants such as an intestinal graft; and various orthopedic implants such as artificial joints.

In one aspect, embodiments of the polymer composition can be used for the fabrication of a vascular implant such as a vascular graft which has an inner layer comprising the first polymer backbone and outer or tissue contacting layer comprising the second polymer backbone. The first layer provides the graft with selected mechanical properties including tensile strength, hoop strength and compliance or elasticity (radial and longitudinal) matched to the native arterial tissue at each anastomosis so the graft can expand and contract with each arterial pulse in substantially the same manner as native tissue. The outer layer provides a non-thrombogenic blood contacting layer which also serves as substrate for the attachment of endothelial and other cells. In time, the outer layer degrades and is replaced by a neo-intimal native layer comprising endothelial cells and other cells. In particular embodiments, the outer layer can also comprise various cell adhesion and migration promoting polypeptides such as MAP and P-15. Such cell attachment promoting polypeptides can be configured to promote the attachment and growth of a substantially confluent layer of endothelial or other cells on the outer layer so to enhance and maintain the long term biocompatibility of the neo-intimal layer.

In other aspects, embodiments of the invention can also be used in the fabrication of various surgical supporting membranes or meshes used for the repair or buttressing of anatomical structures such as the abdominal wall, peritoneal membrane, and the myocardial wall or other portion of the heart. In specific applications, embodiments of the invention can be used in for the repair of various atrial septal defects such as a patent ductus. In these embodiments, the mesh or membrane can comprise an inner or core layer comprising the first polymer backbone and outer or overlying layer comprising the second polymer backbone. The inner or core layer provides the membrane with selected mechanical properties such as strength, and stiffness so that it can provide mechanical support to a selected tissue site while the outer layer provides a biocompatible tissue contacting layer which also serves as a substrate for the attachment of native cells, collagen and other native proteins. In time, the outer layer degrades and is replaced by a neo-biological layer composed of native cells and collagen and is still supported by the inner layer providing the implant its desired mechanical properties. As described above, the outer layer can also include cell attachment promoting polypeptides to promote the development of a confluent endothelial or other cellular layer so as to enhance and maintain the long term biocompatibility of the neo-biological layer.

In still another aspect, embodiments of the invention can also be used in the fabrication of an intestinal graft used for the repair and support of a surgical anastomosis such as may result from a bowel resection. In these embodiments, the graft can comprise a central portion comprising the first polymer backbone and adjacent extending side portions comprising the second polymer backbone. The central portion provides the radial mechanical support and longitudinal strength to the anastomotic junction, while the end portion portions provide a substrate for the attachment of native tissue and can include the cell attachment promoting polypeptides as can the central portion. In time, the end portions degrade and are replaced by native tissue while the central portion remains permanently or for a much longer period of time (e.g., months) so as to provide the necessary mechanical support. Further description of various biodegradable intestinal anastomotic grafts/scaffolds is found in U.S. patent application Ser. No. 12/181,244 which is fully incorporated by reference herein.

In an exemplary embodiment of a method for using one or more embodiments of a medical implant comprising a first and second polymer backbone where the second polymer backbone has a faster rate of biodegradation then the first polymer backbone (e.g., 100 or 1000 times faster), the implant is implanted at an implant site in the body, for example, at an artery or a section of the large or small intestine and the first and second polymer backbones are biodegraded in vivo for a period of time by mechanisms such as hydrolysis and other biochemical reactions within the body. The implant may comprise a stent such as vascular stent, or a graft such as a vascular graft. During a period of biodegradation which can be days, months or years, a substantial portion of the second polymer backbone is degraded while a sufficient amount of the first polymer backbone remains so as to provide structural support to the implant. Desirably the amount of structural support is such that the implant does not mechanically fail (e.g., dissection, tear, shear, rip etc) during the period of biodegradation. Also desirably, the during the period of biodegradation, a sufficient amount of the first of the polymer backbone remains so as to maintain a mechanical property of the implants such as tensile strength, hoop strength, stiffness, elasticity and like properties. In particular embodiments, during a selected period of biodegradation (e.g., days, weeks, months) 50% or more by weight of the second polymer backbone can be degraded while 50% or more by weight of the first polymer backbone remains. Also, the second polymer backbone can be configured such it not only degrades, but also promotes the attachment of a tissue layer which can include both cells (e.g., endothelia cells) and proteins (e.g., collagen). In such embodiments the second polymer backbone can be comprise or be attached to a cell adhesion and migration promoting polypeptide (or CAMP), such as MAP, or P-15. The CAMP can also be attached to the first polymer backbone and can be used to not only promote attachment of cells to the implant, but also to promote the migrations of cells on the implant surface to as to produce a confluent layer of cells, e.g., a confluent layer of endothelial or smooth muscle cells. Further, during the period of biodegradation, the second polymer backbone can also be replaced or substantially replaced with the tissue layer. Again, at least a portion of the first polymer backbone remains (e.g., greater than 25, 50% etc.) so as to provide sufficient structural support to the implant so that the implant does not mechanically fail (e.g., in the case of a vascular graft, dissect from hoop stress forces resulting from arterial blood pressure) or otherwise cease to perform its intended function due to changes in mechanical properties (e.g., changes in elasticity for vascular grafts).

In many embodiments, the first and second polymer backbones can comprise separate first and second polymeric layers respectively. The second polymer layer can be configured as a tissue or blood contacting layer and can be configured to degrade in surface eroding fashion. Further, the second polymer backbone be selected or otherwise configured to be non-thrombogenic sot that there is minimal or no formation of thrombus on a surface of the implant comprising the second polymer backbone.

Further details of these and other embodiments and aspects of the invention are described more fully below with reference to the attached figures.

BRIEF DESCRIPTION OF THE DRAWINGS

FIG. 5a shows the advanced degradation of the second layer; and FIG. 5b shows the replacement of the second layer with a neo-cellular layer.

DETAILED DESCRIPTION OF THE INVENTION

Figure 1:
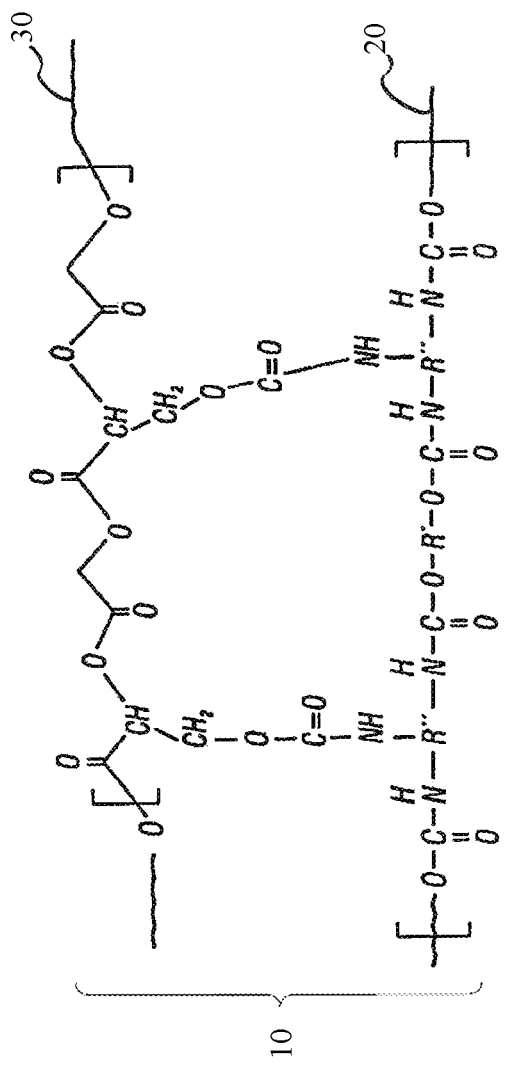
FIG. 1 shows an embodiment of a polymer composition comprising first and second polymer backbones which are cross linked.

Referring now to FIGS. 1-6, embodiments of the invention provide polymer compositions 10, comprising at least a first and second polymer backbone 20 and 30. As is discussed below, additional numbers of backbones (not shown) are also contemplated. Composition 10 can be used in the fabrication of a number of medical implants 40 such as vascular grafts, stents, shunts and various surgical membranes. First and second backbone 20 and 30 can be selected to have different materials properties so as to provide different material properties and functionality to implant 40. For example, in many embodiments, backbone 20 can be configured to provide various mechanical properties to implant 40 (e.g., hoop strength and elasticity, etc), while backbone 30 is configured to promote the attachment and growth of various cells and protein materials. In particular embodiments, backbone 20 is selected and configured so as to provide a supporting scaffold 50 for implant 40, which may remain for all or a substantial portion of the life of the implant.

In many embodiments, backbones 20 and 30 are selected such that backbone 20 has a first rate of biodegradation which is slower than the rate of biodegradation of second backbone 30. Bio degradation of backbones 20 and 30 can proceed by various chemical reactions of the backbones with body tissue and fluids, such as hydrolysis, or enzymatic degradation. For convenience, the term "biodegradation" will now be referred to as "degradation." Owing to the differences in rates of degradation, the second polymer backbone 30 degrades while substantially all or a significant portion of polymer backbone 20 remains to provide structural support to implant 40, for example through use of scaffold 50. Desirably, a sufficient amount of backbone 20 remains to provide sufficient structural support such that implant 40 does not tear, dissect, shear, rip or otherwise mechanically fail. This can be achieved by using materials for backbone 20, such as polyurethane with selected strength (e.g., tensile strength, hoop strength, etc) and degradation rates.

In various embodiments, the second polymer backbone 30 can be configured to degrade over a period of day, weeks, months or even years. During this time, the degradation rate of the first polymer backbone 20 is desirably sufficiently slower than that of second polymer backbone 30 such that first polymer backbone 20 maintains enough of its structure to provide a scaffold 50 for the implant or otherwise provide a minimum level of structural support for the implant. In various embodiments, the degradation rate of the first polymer backbone 20 can be 10, 50, 100, 500 or even a 1000 times slower than the degradation rate of the second polymer backbone 30. The degradation rates of the first and second backbones 20 and 30 can be selectable based on one or more factors, known as the "degradation factors" described below. These factors may used to select degradation rates for first and second polymer backbones 20 and 30 (including ratios between the rates) such that substantially all or a significant portion of first polymer backbone 20 remains after substantially all or a significant portion of second polymer backbone 30 has degraded.

In some embodiments, composition 10 can comprise a third, fourth or even a fifth polymer backbone, with still additional numbers of backbones contemplated. Also, one or more monomeric substances can also be included. These additional polymer backbones or monomers can be selected for their particular mechanical and material properties (e.g., strength, elasticity, etc) or for their effect on the other polymer backbones, e.g., such as the use of plasticizer to increase elasticity.

Figure 2:
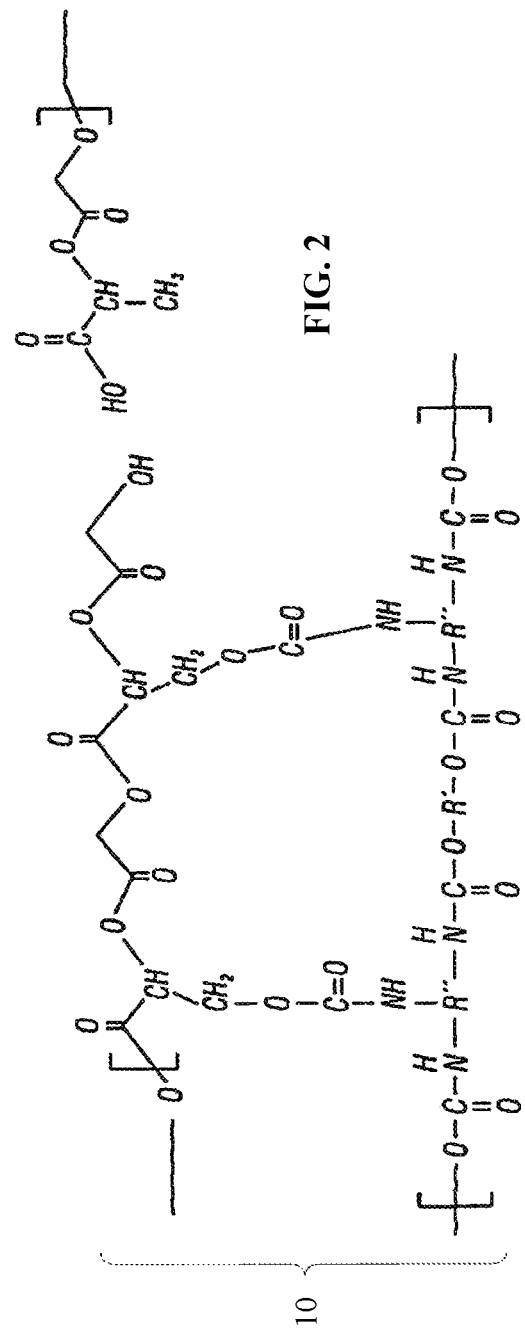
FIG. 2 illustrates degradation of the second polymer strand of the composition of FIG. 1.
Figure 5A:
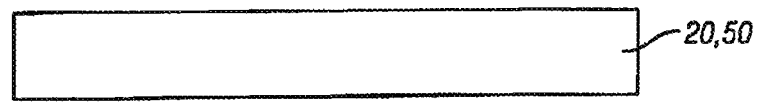
FIGS. 5a and 5b are lateral views illustrating the time course of biodegradation of the implant of FIG. 4.
Figure 5B:
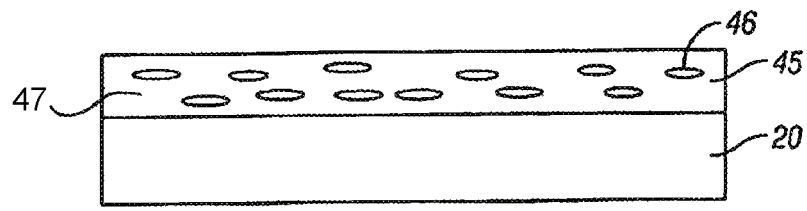
Figure 6:
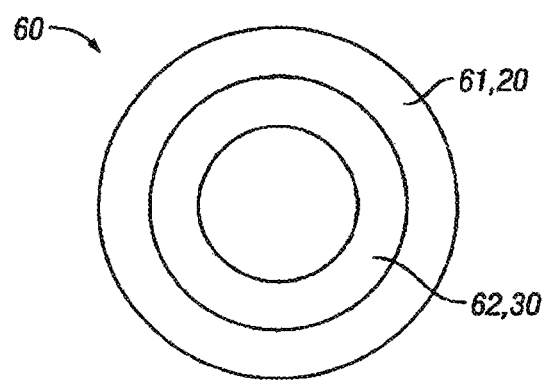
FIG. 6 is a cross sectional view showing an embodiment of a vascular graft fabricated from a polymer composition having differentially degradable polymer backbones.

As described above, backbone 30 is degraded in the body by various reactions such as hydrolysis (e.g., hydrolytic degradation). An example of hydrolytic degradation of a PGLA backbone 30 is shown in FIG. 2. In this example, degradation occurs by cleavage between a lactic acid residue and glycolic acid residue. Over time, all or substantially all, or other substantial portion (e.g., greater than 50, 60 or 75% by weight) of backbone 30 is degraded as is shown in FIG. 5b. During or after the process of degradation, backbone 30 can be replaced by a neo-biological tissue layer 45 (also called tissue layer 45) which can comprise various cells 46, collagen and other related proteins 47 which are deposited and attach to backbone 30. In some embodiments, backbone 30 can be configured to have surface properties (e.g., surface tension, hydrophilicity, etc.) and binding sites such that cells 46 can initially attach to backbone 30 and then migrate and grow onto exposed backbone 20. An example of such a backbone 30 can include MAP or a P-15 polypeptide described in herein. In these and related embodiments, backbone 30 can thus function as a substrate 31 for the attachment of cells, proteins and other biological material.

In many embodiments, the first polymer backbone 20 is configured to have a substantially stable structure within the body during the life of implant 40, or otherwise have a substantially slower rate of biodegradation such that scaffold 50 remains substantially in place after second backbone 30 has completely or otherwise substantially degraded. Scaffold 50 can be configured to enhance one or more selected mechanical properties of implant 40 so as improve one or more of its function, reliability and durability over the life of the implant. These properties can include: mechanical strength such as tensile strength, bending strength and hoop strength; elasticity and yield strength; and fracture resistance. In particular embodiments, these properties can be tailored to reduce the likelihood of mechanical failure of the implant (e.g., increased hoop strength to reduce the risk of dissection for vascular grafts). The composition of first backbone 20 within scaffold 50 can be configured such that the scaffold serves to maintain a minimum level of structural rigidity/support of implant 40 during the period of degradation of the second backbone 30 or even longer. This allows implant 40 to continue to perform its intended functions during the period of degradation and preferably throughout the entire life of the implant. For example, in the case of a GI graft/scaffold, providing support for a surgical anastomosis in the GI tract or for the case of a stent, maintaining the patency of an artery or organ duct until such time the second backbone is replaced with cellular tissue or if necessary for the life of the implant.

In many embodiments, backbones 20 and 30 can be cross linked, such that one or more functional groups in backbone 20 are chemically bound to functional groups in backbone 30. In various embodiments, cross linking can be achieved by configuring or modifying backbones 20 and 30 to have one or more active sites. The active sites can activated by treating backbones 20 and 30 with one or more of the following treatments: plasma treatment (e.g., an argon plasma), UV radiation, e-beam or other radiation or heat (e.g., thermal treatment). The treatment and formation of cross links is also known as "curing." One or more catalysts or curing agents can be added to a solution containing polymer backbone s 20, 30 (or other polymer backbone) so as to either initiate and/or accelerate the cross linking process. The curing agent can be selected based on the selection of the individual polymer backbones 20 and 30 as well as the particular curing method (e.g. thermal vs., UV).

In many embodiments, the first polymer backbone 20 is configured so as to have a substantially stable structure within the body during the life of implant 40, or otherwise may have a substantially slower rate of biodegradation such that scaffold 50 is still substantially in place after second backbone 20 has completely degraded. As discussed herein, the first and second backbones may also have selected amount of cross linking with the amount of cross linking selected to slow or otherwise control the rate of biodegradation of one or both of the first or second backbones. Over time, the second backbone is broken down by chemical reactions within the body such as hydrolysis, while substantially all or at least a portion of the first backbone remains. In particular embodiments, 25, 50, 75, 80, 90, 95, 99 or 100% of the first polymer backbone may remain over extended periods of time, e.g., years. The rate of degradation can be controlled by one or more of the following factors (the "degradation factors"): i) the chemical nature of the first and second backbone and the physical properties resulting therefrom (e.g., the types of chemical linkages within the backbone and the functional groups attached to the backbone; crystallinity, hydrophilicity, etc); ii) the weight ratio of the first backbone to the second backbone; iii) the presence or absence of cross-linking between the backbones; and iv) an amount of cross linking of the backbones, with greater amounts of cross linking providing slower rates of degradation. One or more of these factors, such as the amount of cross linking, can be selected to control one or both the rates of degradation of the first and the second backbone 20 and 30.

In various embodiments, the degradation rate of first polymer backbone 20 can range from about 0.01 to about 99% of the degradation rate of second polymer backbone 30 with specific embodiments of 0.1, 1, 2, 5, 10, 20 and 50%. Particular degradation rates of one or both backbones 20 and 30 can be selected for particular implant sites, for example faster rates can be selected for intestinal grafts and slower rates for vascular grafts. The ratio of the degradation rates can also be tailored to the particular implant site. In particular embodiments, the degradation rate of backbone 30 can be in the range of 10 to 100 times faster than the degradation rate of backbone 20, with even larger ratios contemplated (e.g., 500 to 1000 times faster). Also, the faster the absolute degradation rate of second backbone 30, the slower the degradation rate of backbone 20 can be relative to the degradation rate of backbone 30. For example, if backbone 30 degrades in a matter of days, the degradation rate of backbone 20 can be less than 1% of that of backbone 30.

In various embodiments, backbone 20 can comprise polyurethanes, polyurethane urea, polyethylenes, polypropylenes, polystyrenes, polysiloxanes and mixtures thereof, while backbone 30 can comprise polyglycolic acid (PGA), polylactic acid (PLA); polyglycolic lactic acid (PGLA), polyorthoesters, poly(dioxanone) poly(anhydrides), poly(trimethylene carbonate), polyphosphazenes and various polymer comprising cell adhesion and migration promoting peptides such as multiple armed polypeptides (MAP), P-15 and combinations thereof. Further description of MAP and P-15 are found in U.S. patent application Ser. No. 10/664,697 which is incorporated by reference herein in its entirety. A therapeutic agent, such as an antibiotic or a steroid, may be included in a layer which comprises backbone 30.

In various methods for fabrication of composition 10, polymer backbone 20 and polymer backbone 30 can be added to a solution in which they are both backbones are soluable (e.g., both backbones have functional groups which have an affinity for the solvent, e.g., by ionic forces,). Suitable solvents can include various organic and polar solvents known in the art including, acetones and methyle ether ketones. In some embodiments, a third, or fourth or fifth polymer backbone can be added to the solution with still additional numbers contemplated as is described above. Implant 40 can then be formed from the solution of one or using various polymer processing methods know in the art such as casting, molding, injection molding, extrusion, blow film extrusion and other methods known in the art. Once implant 40 is formed, the solvent can then be allowed to evaporate off. In some embodiments, the implant can be formed by dip coating a structure such as a vascular graft or tubing into the solution and then allowing the solvent to evaporate off In embodiments where the two backbones are cross linked (e.g., chemically bound to each other as is described herein), cross linking, also known as curing, can be performed during or after formation of the implant using various methods known in the art including through use of one or more of the following: the application of heat, the application of UV light, radiation (e.g., e-beam radiation) or through the addition of one or more cross linking agents or catalysts allowing for room temperature curing. The amount of cross linking can be controlled by the amount/duration of heat and/or UV light, radiation application as well as the amount of the cross linking agent added. Increased amounts of cross linking be used for implants requiring higher amounts of strength (e.g., such hoop strength for a stent) or stiffness.

In preferred embodiments, composition 10 comprises a polymer backbone 20 that comprises a polyurethane (PU) and polymer backbone 30 comprises PGA or PGLA. As shown in FIG. 1, the PU backbone typically contains one or more R groups (as is known in the art) located between the urethane bonds where the R groups for example, comprise an aliphatic or aromatic group. In various methods of fabrication of composition of 10, these two polymers can be mixed together by dissolving them in a solvent in which they are both soluable such as Tetrahydrofuran (THF) (other solvents are also contemplated). In specific embodiments, the weight of added polymer (both PU and PGLA) in the THF solution can be in the range from about 15 to 20% (wt % solute/% solvent). The ratio of PU to PGLA or PGL can be in the range of 1:20 to 20:1, with specific embodiments of 1:4, 2:3, 1:1, 3:2 and 4:1. Higher amounts of PU can be selected for application requiring increased mechanical strength such as tensile strength for GI applications and hoop strength for vascular application. Example 1 provides a table listing of mechanical properties for different ratios of PU to PLGA. The data show that even small amounts of PU (e.g., 20%) can increase the stiffness of the mixture.

In various embodiments of composition 10 which comprises a PU polymer backbone 20 and a PGLA polymer backbone 30, the two backbones can be cross linked. This can be achieved by several different approaches. In one approach, one or more of the methyl side groups of e PGLA backbone can derivatized with one or more constituents reactive groups as hydroxy, amino, thio, or carboxy group so that the reactive group will form a cross link with the PU backbone. In an embodiment shown in FIG. 1, one or more methyl groups of the PGLA backbone 30 can be derivatized to hydroxyl groups which form cross links with an isocynate-side group of the PU backbone. Derivitization can be achieved for example, by chemical modification of the PGLA monomer prior to forming the polymer of PGLA, or after the polymer has been formed. In another approach, the formed composition 10 of PU backbone 20 and PGLA backbone 30 can be treated with e-beam radiation. In still another approach, a first layer of PGLA can be plasma treated with, for example, an argon plasma so to derivatize one or more functional groups and then the treated layer can be dip coated in a solution of PU polymer.

Figure 3:
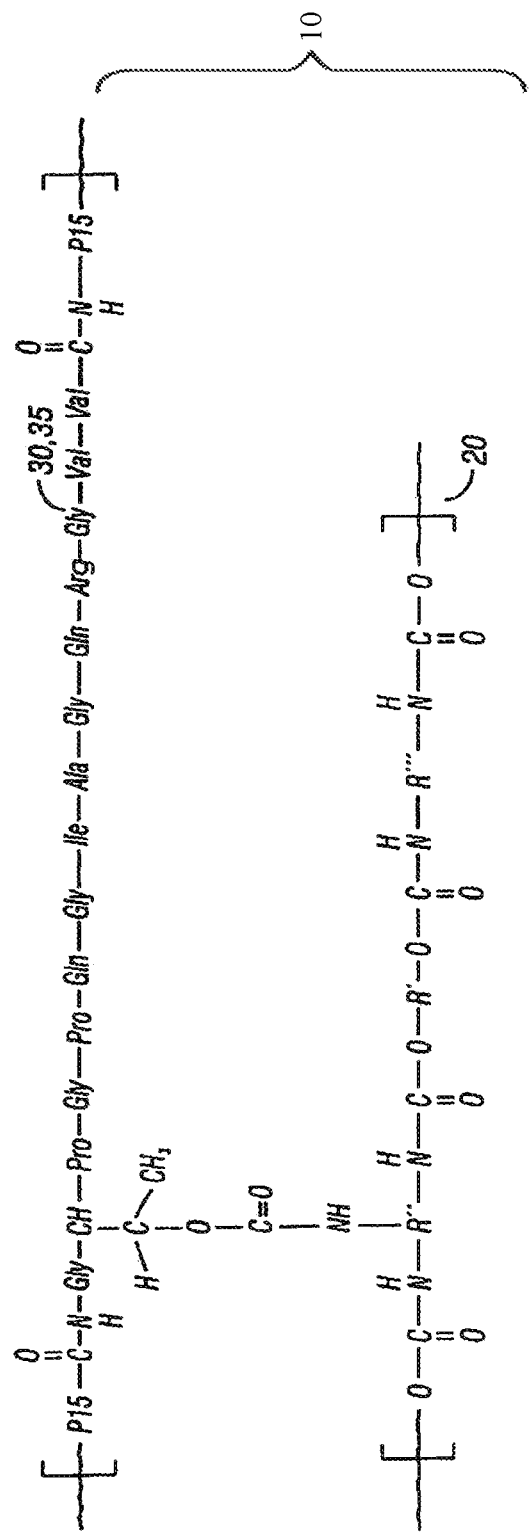
FIG. 3 shows an embodiment of a polymer composition comprising a polyurethane backbone cross linked to a P-15 polypeptide.
Figure 4:
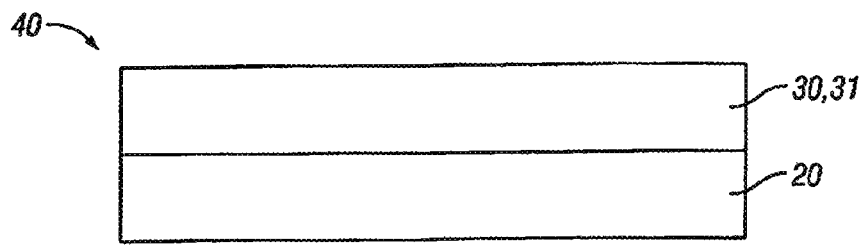
FIG. 4 is a lateral view showing an embodiment of an implant having a first and second polymer layer, the first layer comprising the first polymer backbone, the second layer comprising the second backbone.

In other embodiments, composition 10 can comprises a PU polymer backbone 20 and a polymer backbone 30 containing a cell adhesion and migration promoting peptide 35 such as MAP or P-15 as well as fragments, variants and analogues thereof (which can be derived and synthesized using various functional testing and synthesis methods known in the art). Cell adhesion and migration promoting peptide (CAMP peptide) 35 serve to promote the adhesion and subsequent migration of various cells to a surface of implant 40 such as endothelial cells. This in turn, serves to promote the formation of a confluent cellular layer on implant 40. The formation of confluent layers on the implant 40, such as a vascular graft enhances the long term biocompatibility of the implant. One embodiment of a polymer backbone 30 containing a CAMP peptide is shown in FIG. 3. In this embodiment, the CAMP peptide comprises P-15. The CAMP peptides can be cross linked to the PU backbone through several approaches. In one approach, shown in the embodiment of FIG. 3, the P-15 peptide is cross linked via the hydroxyl group of its tyrosine residue to an isocyanate side chain of the PU backbone 20. Other sites for cross linking on the P-15 peptide can include glutamine and arginine. Additionally, other CAMP peptides are also contemplated such as MAP described herein as well as variants and fragments thereof.

Embodiments of the polymer composition 10 described herein can be used for the fabrication of a number of biodegradable medical implants. These can include sutures and other closure devices (e.g., a butterfly device), vascular implants such as vascular grafts (e.g., an aortic graft), arterial stents (e.g., coronary arterial or femoral stents), heart valve; gastro-intestinal implants such as an intestinal graft used for the repair of a surgical anastomosis; biliary and other stents, various orthopedic implants such as artificial, hips and knee joints and various supporting membranes and meshes used for surgical reconstruction. Composition 10 be used for all or a portion of implant 40 such that the implant 40 has biodegradable regions and non biodegradable regions.

In one aspect, embodiments of composition 10 can be used in the fabrication of a vascular graft 60 which has outer layer 61 comprising first polymer backbone 20 and an inner or tissue/blood contacting layer 62 comprising second polymer backbone 30. Outer layer 61 provides graft 60 with selected mechanical properties including tensile strength, hoop strength and compliance or elasticity (radial and longitudinal) which can be matched to the native arterial tissue at each anastomosis so the graft can expand and contract with each arterial pulse in substantially the same manner as native tissue. The inner layer 62 provides a non-thrombogenic blood contacting layer which also serves as a substrate for the attachment of endothelial and other cells 46. In time, inner layer 62 degrades and is replaced by a neo-intimal layer 45 comprising endothelial and other cells 46. In particular embodiments, the inner layer 62 can also comprise various CAMP polypeptides such as MAP and P-15 which can be attached to polymer backbone 30 using approaches described herein. They may also be attached to backbone 20 as well. Such CAMP polypeptides can be configured to promote the attachment and growth of a substantially confluent layer of endothelial or other cells on the inner layer 62. Having such a confluent layer of cells serves to enhance and maintain the long term viability and biocompatibility of the neo-intimal layer 45 and in turn, graft 60 or other implant 40. Thus in use, embodiments of the invention having such CAMP polypeptides (comprising one or both of backbones 20 and 30) serve to enhance the long term biocompatibility and life of graft 60 or other implant 40.

EXAMPLES

Various embodiments of the invention will now be further illustrated with reference to the following examples. However, it will be appreciated that these examples are presented for purposes of illustration and the invention is not to be limited by these specific examples or the details therein.

Example I

Various mixtures of PU and PGLA were fabricated by mixing amounts of commercially obtained PU and PGLA in a solution of Tetrahydrofuran (99.5%). The amounts of added PU and PGLA were calculated to achieve weight ratios in the range from 20:80 to 80:20 Pu to PGLA. Various samples of the polymer composition were then formed into film using a glass plate having approximate dimension of: 6 cm (length), 1 cm (width) and, 1 mm (thickness). The dimensions of the formed film were then measured and used in the stiffness calculations. The films were then attached to Chatillion tensile tester and pulled to failure at rate of 1 inch/minute. Tensile strength was determined as the maximum pull strength and stiffness was calculated. The resulting tensile strength and stiffness data are tabulated in Table 1.

TABLE 1

| Sample # | % PU | % PGLA | Tensile Strength (lbs) | Stiffness (lbs/inch) |
| --- | --- | --- | --- | --- |
| 1 | 0.0% | 100.0% | 0.5 | 1.2 |
| 2 | 20.0% | 80.0% | 0.7 | 4.1 |
| 3 | 30.1% | 69.9% | 1.2 | 3.1 |
| 4 | 49.6% | 50.4% | 1.7 | 3.0 |
| 5 | 69.8% | 30.2% | 2.1 | 4.8 |
| 6 | 79.9% | 20.1% | 3.8 | 4.4 |
| 7 | 100.0% | 0.0% | 7.3 | 3.4 |

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the medical implants described herein can be shaped and sized for implantation in any number of locations in the body. They can also be configured to have material selectable rates of degradation and other material properties adapted for the particular implantation site such as the vascular system including veins and arteries, GI tract, bone, etc.

Elements, characteristics, or acts from one embodiment can be readily recombined or substituted with one or more elements, characteristics or acts from any other embodiment to form numerous additional embodiments within the scope of the invention. Moreover, elements that are shown or described as being combined with other elements, can, in various embodiments, exist as standalone elements. Hence, the scope of the present invention is not limited to the specifics of the described embodiments, but is instead limited solely by the appended claims.

What is claimed is:

1. A method for using a biodegradable medical implant in the human body, the method comprising:
   implanting a medical implant at an implant site in the body, the implant comprising a polymer composition comprising a mixture of a first polymer backbone and a second polymer backbone cross-linked to the first polymer backbone, the first polymer backbone having a first rate of biodegradation and comprising a polyurethane, the second polymer backbone having a second rate of biodegradation faster than the first rate of biodegradation and comprising polyglycolic acid (PGA) or polyglycolic lactic acid (PGLA), wherein a weight ratio of polyurethane to PGLA or PGA in the composition ranges from about 20:80 to 80:20 and a stiffness of the implant ranges from about 3.0 to 4.8 pounds per inch; and
   degrading the first and second polymer backbones for a period of time at the implant site, wherein the second polymer backbone degrades at a faster rate than the first polymer backbone such that the first polymer backbone provides a scaffold for the implant that is maintained while the second polymer backbone degrades.

2. The method of claim 1, wherein the implant is a stent, a biliary stent, a vascular stent or a coronary artery stent.

3. The method of claim 1, wherein the implant is a graft, an intestinal graft, a vascular graft, an arterial graft or an aortic graft.

4. The method of claim 1, wherein during the period of biodegradation time, a sufficient amount of the first backbone remains so as to maintain a mechanical property of the implant.

5. The method of claim 4, wherein the mechanical property is a least one of tensile strength, bending strength, tensile stiffness, bending stiffness, elasticity or fracture resistance.

6. The method of claim 1, wherein during the period of biodegradation time, a sufficient amount of the first backbone remains so as to maintain a minimum level of structural support for the implant such that the implant does not mechanically fail.

7. The method of claim 1, wherein during the period of biodegradation time, a substantial portion of the second polymer backbone is degraded while at least a portion of the first polymer backbone remains.

8. The method of claim 7, wherein at least 50% by weight of the second polymer backbone is degraded.

9. The method of claim 7, wherein at least 50% by weight of the first polymer backbone remains.

10. The method of claim 1, wherein the second polymer backbone is configured to promote attachment of a tissue layer to a surface of the implant comprising the second polymer backbone, the method further comprising:
    using the second polymer backbone to promote attachment of the tissue layer to the surface of the implant.

11. The method of claim 10, further comprising:
    degrading a substantial portion of the second polymer backbone while at least a portion of the first polymer backbone remains so as to maintain a minimum level of structural support for the implant such that the implant does not mechanically fail.

12. The method of claim 11, wherein at least 50% by weight of the second polymer backbone is degraded.

13. The method of claim 11, wherein at least 50% by weight of the first polymer backbone remains.

14. The method of claim 11, wherein the scaffold provided by the first polymer backbone provides a scaffold for attachment and support of the tissue layer.

15. The method of claim 10, wherein the tissue layer comprises endothelial cells, smooth muscle cells, platelets, proteins or collagen.

16. The method of claim 10, wherein the implant comprises a cell adhesion and migration promoting polypeptide (CAMPP) attached to at least one of the first or the second polymer backbones.

17. The method of claim 16, wherein the CAMPP is a MAP or P-15 polypeptide.

18. The method of claim 16, further comprising:
    using the CAMPP to generate a substantially confluent cellular layer on the surface of the implant.

19. The method of claim 18, wherein confluent cellular layer comprises endothelial cells.

20. The method of claim 1, wherein the first and second polymer backbones comprise separate first and second polymeric layers of the medical implant, the second polymeric layer being a tissue or blood contacting layer.

21. The method of claim 20, wherein the second polymeric layer degrades in a surface eroding fashion.

22. The method of claim 1, wherein the second rate of biodegradation is at least ten times faster than the first rate of biodegradation.

23. The method of claim 22, wherein the second rate of biodegradation is at least one hundred times faster than the first rate of biodegradation.

24. The method of claim 1, wherein the first polymer backbone has a substantially stable structure within the body during the life of the implant in the body.

25. A method for using a biodegradable medical implant in the human body, the method comprising:
    implanting a medical implant at an implant site in the body, the implant comprising a polymer composition comprising a mixture of a first polymer backbone and a second polymer backbone cross-linked to the first polymer backbone by a urethane linkage between an isocyanate side group on the first polymer backbone and a methylene side group on the second polymer backbone, the first polymer backbone having a first rate of biodegradation and comprising a polyurethane, the second polymer backbone having a second rate of biodegradation faster than the first rate of biodegradation and comprising polyglycolic acid (PGA) or polyglycolic lactic acid (PGLA), wherein a weight ratio of polyurethane to PGLA or PGA in the composition ranges from about 20:80 to 80:20; and
    degrading the first and second polymer backbones for a period of time at the implant site wherein the second polymer backbone degrades at a faster rate than the first polymer backbone such that the first polymer backbone provides a scaffold for the implant that is maintained while the second polymer backbone degrades.

26. The method of claim 25, wherein at least 50% by weight of the second polymer backbone is degraded.

27. The method of claim 25, wherein the scaffold provided by the first polymer backbone provides for attachment and support of a cellular layer.

28. The method of claim 27, wherein the cellular layer comprises endothelial cells or smooth muscle cells.

29. The method of claim 25, wherein a stiffness of the implant ranges from about 3.0 to 4.8 pounds per inch.

* * * * *